US008543188B2

(12) United States Patent
von Jako et al.

(10) Patent No.: US 8,543,188 B2
(45) Date of Patent: Sep. 24, 2013

(54) METHOD AND APPARATUS FOR CALIBRATING MEDICAL DEVICES

(75) Inventors: Ron Andrew von Jako, Melrose, MA (US); Daniel Eduardo Groszmann, Cambridge, MA (US)

(73) Assignee: General Electric Company, Schenectady, NY (US)

( * ) Notice: Subject to any disclaimer, the term of this patent is extended or adjusted under 35 U.S.C. 154(b) by 1315 days.

(21) Appl. No.: 11/550,010

(22) Filed: Oct. 17, 2006

(65) Prior Publication Data

US 2008/0161679 A1    Jul. 3, 2008

(51) Int. Cl.
*A61B 5/05* (2006.01)
(52) U.S. Cl.
USPC .......................... 600/424; 606/130; 600/407
(58) Field of Classification Search
USPC ................. 600/410, 425, 437, 414, 426, 424, 600/427; 348/25, 113, 116, 77, 141, 142, 348/169; 382/103
See application file for complete search history.

(56) References Cited

U.S. PATENT DOCUMENTS

| 6,175,756 | B1 | 1/2001 | Ferre et al. |
| 6,235,038 | B1 * | 5/2001 | Hunter et al. ................. 606/130 |
| 6,925,339 | B2 * | 8/2005 | Grimm et al. ................... 700/59 |
| 6,932,823 | B2 * | 8/2005 | Grimm et al. ................. 606/130 |
| 2005/0203539 | A1 * | 9/2005 | Grimm et al. ................... 606/99 |

* cited by examiner

*Primary Examiner* — Long V. Le
*Assistant Examiner* — Nicholas Evoy
(74) *Attorney, Agent, or Firm* — Andrus, Sceales, Starke & Sawall, LLP

(57) ABSTRACT

A calibration apparatus for a medical device is disclosed herein. The calibration apparatus includes a locating member configured to locate a first predetermined portion of the medical device. The calibration apparatus also includes a calibration member positioned relative to the locating member such that, when the calibration apparatus is attached to the medical device, the calibration member aligns with a second predetermined portion of the medical device. A corresponding method for determining the location of the second predetermined portion of the medical device is also provided.

20 Claims, 3 Drawing Sheets

ID OF THE INVENTION

This disclosure relates generally to a method and apparatus for calibrating medical devices used in computer navigated surgical procedures.

BACKGROUND OF THE INVENTION

In minimally invasive surgical procedures, access to the body is obtained through one or more natural openings or small percutaneous incisions. Medical devices are inserted through these openings and directed to a region of interest within the body. Direction of the medical devices through the body is facilitated by navigation technology wherein the real-time location of a medical device is measured and virtually superimposed on an image of the region of interest. The image may be a pre-acquired image, or an image obtained in near real-time or real-time using known imaging technology such as X-ray, computed tomography (CT), magnetic resonance (MR), or ultrasound (US).

Conventional navigation technology measures the location and orientation of a remote unit attached to the medical device relative to a reference unit. Patient motion can be taken into account by rigidly mounting the reference unit directly onto the patient. A reference unit attached in this manner is also referred to as a dynamic reference because it moves along with the patient.

The remote unit is typically attached to a proximal end of the medical device, however, the location and orientation of the distal end of the medical device is often of primary importance. It is therefore necessary to determine with a high degree of precision the location and orientation of the distal end of the medical device relative to the remote unit. This determination is generally obtained by calibrating the location of the distal end or tip with respect to the remote unit. Tip calibration is typically performed by placing the tip of the medical device in a fixed location such as a dimple on the reference unit.

The problem is that some instruments do not have a well-defined tip such as aspirators, which have a blunt end or a ring curette that has an annular working end instead of a tip. For calibrating trajectory, one known technique is after calibrating the instrument tip, the user calibrates a "back-tip". By connecting the instrument's "front tip" with a "back tip", the trajectory is defined. Again, the problem with calibrating the trajectory, may be the lack of a well defined back-tip.

BRIEF DESCRIPTION OF THE INVENTION

The above-mentioned shortcomings, disadvantages and problems are addressed herein which will be understood by reading and understanding the following specification.

In one embodiment, a calibration apparatus that is removably attachable to a medical device is provided. The calibration apparatus includes a locating member configured to locate a first predetermined portion of the medical device. The calibration apparatus also includes a calibration member positioned relative to the locating member such that, when the calibration apparatus is attached to the medical device, the calibration member aligns with a second predetermined portion of the medical device.

In another embodiment, a navigation system is provided. The navigation system includes a remote unit attachable to a medical device; a process adapted to determine the position and orientation of the remote unit relative to a reference unit; and a calibration apparatus removably attachable to the medical device. The calibration apparatus includes a calibration member adapted to align with a predetermined portion of the medical device, wherein the calibration member can be implemented to calibrate the medical device and thereby determine the location of the predetermined portion relative to the reference unit.

In yet another embodiment, a method for determining the location of a predetermined portion of a medical device is provided. The method includes providing a calibration apparatus having a calibration member; attaching the calibration apparatus to the medical device such that the calibration member aligns with the predetermined portion of the medical device; implementing the calibration member to calibrate the medical device; and removing the calibration apparatus such that the medical device is not encumbered by a permanently attached calibration feature.

In yet another embodiment, a method for tracking the position and orientation of a medical device during a surgical navigation procedure is provided. The method includes removably attaching a calibration apparatus having a calibration member to one end of the medical device; engaging the calibration member with a reference unit; initiating a calibration process; and pivoting the medical device about the calibration member such that the calibration member remains in contact with the reference unit.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
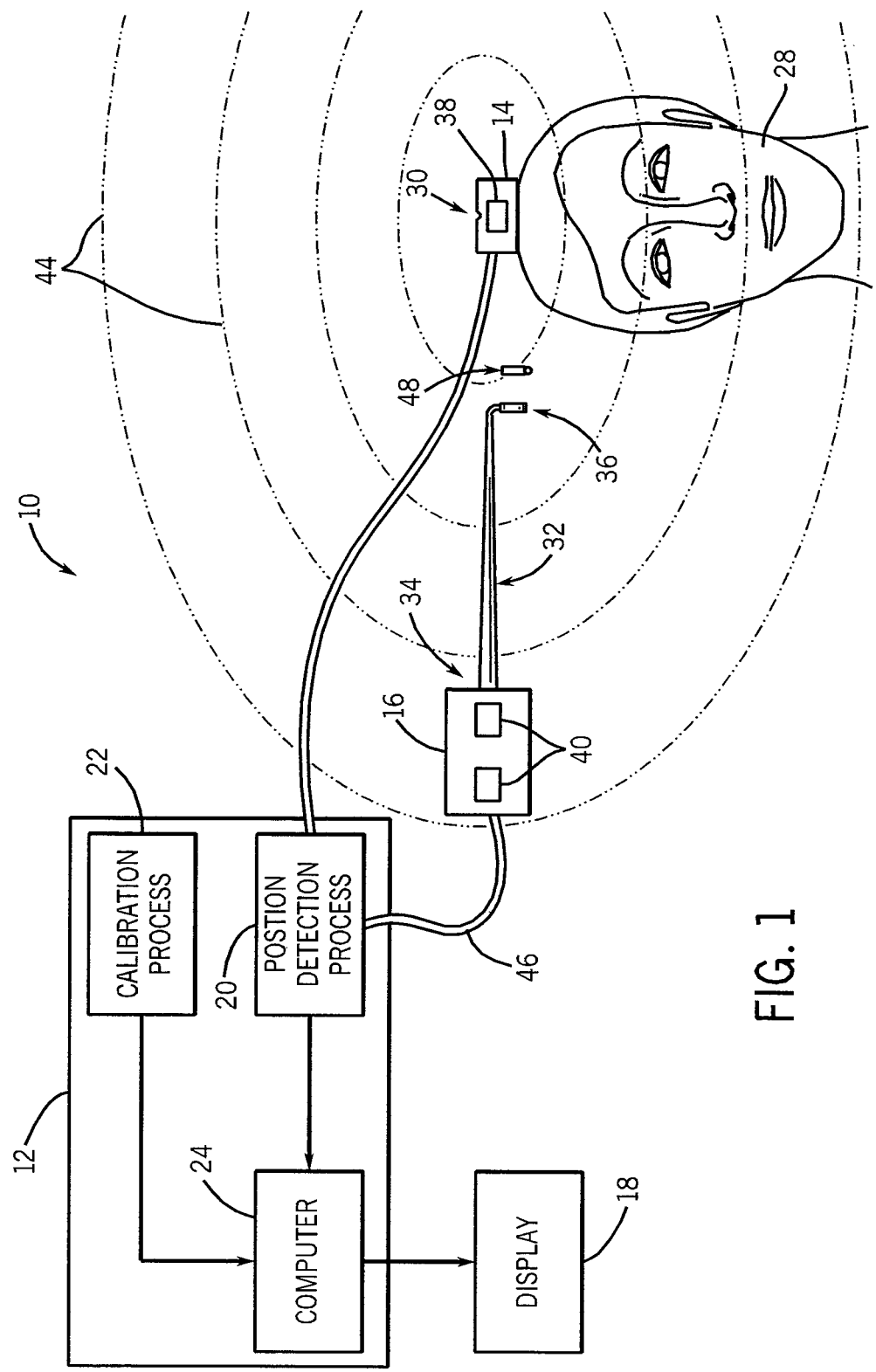
FIG. 1 is a schematic diagram of a navigation system in accordance with an exemplary embodiment.

Referring to FIG. 1, a schematic depiction of a navigation system 10 is shown. It should be appreciated that the navigation system 10 is shown for exemplary purposes, and that the present invention may be implemented with other navigation systems. The navigation system 10 will hereinafter be described as implementing electro-magnetic tracking technology in accordance with an exemplary embodiment. It should, however, be appreciated that the present invention may also be implemented with navigation systems incorporating other tracking technologies such as, for example, optical tracking technologies.

The navigation system 10 is capable of tracking many different types of medical devices during different procedures. Depending on the procedure, the medical device may be a surgical instrument (e.g., a catheter, a guide wire, a debrider, an aspirator, a ring curette, a pointer, a probe, a handle, a guide, etc), a surgical implant (e.g., an artificial disk, a bone screw, a shunt, a pedicle screw, a plate, an intramedullary rod, etc.), or some other device. Depending on the context of the usage of the navigation system, any number of suitable devices may be used. The navigation system 10 includes a control system 12, a reference unit 14, a remote unit 16, a display 18, and a calibration apparatus 48. The control system 12 includes a position detection process 20, a calibration process 22, and a computer 24.

The reference unit 14 may be rigidly attached to the patient 28 in a conventional manner. A reference unit attached in this manner is also referred to as a "dynamic reference" because it moves along with the patient. The reference unit 14 includes a reference feature such as the accepting portion or dimple 30 that is implemented to facilitate calibration as will be described in detail hereinafter. The remote unit 16 is attached to a medical device 32. The medical device 32 will hereinafter be described as being a ring curette, however the present invention may also be implemented with other medical devices. The ring curette 32 defines a proximal end 34 to which the remote unit 16 is attached, and a distal end or tip 36 opposite the proximal end 34.

For purposes of this disclosure, the present invention will be described in accordance with an exemplary embodiment wherein the reference unit 14 includes a field generator 38, and the remote unit 16 includes one or more field sensors 40. It should, however, be appreciated that according to alternate embodiments the reference unit may include the field sensors and the remote unit may include the field generator.

The field generator 38 in the reference unit 14 generates a position characteristic field 44 in an area that includes the target operation site. The field sensors 40 in the remote unit 16 produce sensor signals (not shown) in response to the sensed position characteristic field 44. The sensor signals are transmitted or input into the position detection process 20. The sensor signals may be transmitted via communication line 46, or may be wirelessly transmitted. The position detection process 20 is adapted to determine the position and/or orientation of the remote unit 16 relative to the reference unit 14. For purposes of the present invention, the position of an object refers to its distance from a predefined origin in the X, Y and Z directions, and the orientation of an object refers to the degree to which it is rotated about each of the X, Y and Z axes.

The position and orientation of the distal end 36 of the medical device 32 is generally of primary importance as it is typically the operational end. Therefore, having determined the position and orientation of the remote unit 16 (which is generally attached to the proximal end 34 of the medical device 32) relative to the reference unit 14, it becomes necessary to determine the position and orientation of a point near the distal end 36 of the medical device 32 relative to the remote unit 16. This determination is generally obtained by calibrating the distal end or tip 36 with respect to the remote unit 16. The term "calibration" refers to the process of estimating the position and/or orientation of a first predetermined portion of a medical device (e.g., the tip) relative to a second predetermined portion of the medical device (e.g., the proximal end) or to another device (e.g., the remote unit).

Tip calibration is typically initiated by placing the tip 36 of the medical device 32 in a complementary reference unit feature such as the dimple 30. The calibration process 22 is then initiated and the tip 36 of the medical device 32 is pivoted within the dimple 30. The position detection process 20 transmits position and orientation data to the computer 24 during the calibration process 22. The computer 24 is adapted to implement the position and orientation data transmitted during the calibration process 22 to identify the position and orientation of the tip 36 of the medical device 32. The position and orientation of the tip 36 may then be conveyed to a surgeon in order to facilitate the navigation of the medical device 32.

The position and/or orientation of the distal end 36 of the medical device 32 may, for example, be conveyed via the display 18. According to an exemplary embodiment, a graphical representation of the distal end 36 is superimposed onto a patient image (not shown). More precisely, the graphical representation of the distal end 36 is superimposed onto the portion of the image that corresponds to the actual location of the distal end 36 within the patient 28. The graphical representation may include a dot or cross hairs identifying just the distal end 36, or may include a more complete rendering showing the medical device 32 in detail. The patient image may be a pre-acquired image, or an image obtained in near real-time or real-time using known imaging technology such as X-ray, computed tomography (CT), magnetic resonance (MR), or ultrasound (US).

For some medical devices it may be desirable to calibrate two or more points of interest. As an example, medical devices such as the catheter 60 of FIG. 3 require both "front tip" and a "back tip" calibration in order to convey trajectory information as will be described in detail hereinafter. "Trajectory information" describes the direction along which the catheter guide wire 70 can be extended. The distal end 68 of the catheter 60 may be graphically represented by a solid line connecting a front point and a rear point respectively representing the front tip 72 and the rear tip 74. The trajectory information may be graphically represented by a dashed line extending from the front point in the direction along which the guide wire 70 is extendable.

Tip calibration is potentially less precise where the distal end of the medical device does not have a well-defined tip such as, for example, the ring curette 32 (shown in FIG. 1) which has an annular working end. Similarly, with respect to the catheter of FIG. 3, it may be relatively easy to calibrate the front tip 72, but appreciably more difficult to calibrate the less well defined rear tip 74. A calibration apparatus is therefore provided in order to improve calibration precision for medical devices without a well defined tip. Additionally, a variety of different calibration apparatus configurations may be implemented to accommodate different medical devices, and the calibration apparatuses may be removable such that the medical devices are not encumbered by a permanently attached calibration feature.

Figure 2:
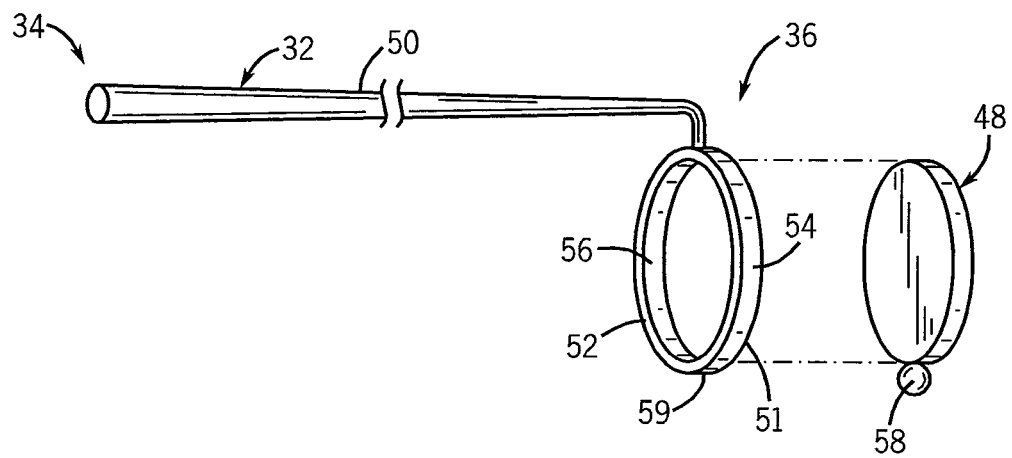
FIG. 2 is a perspective illustration of a ring curette and a schematically depicted calibration apparatus in accordance with an exemplary embodiment.

Referring to FIG. 2, the ring curette 32 is shown in more detail along with a schematic representation of the calibration apparatus 48. The distal end 36 is generally annular and forms an angle of approximately 90 degrees relative to the body 50. The distal end 36 includes an axially defined forward edge 51 that is also generally the cutting edge, and a rearward edge or surface 52 opposite the forward edge 51. The distal end 36 also defines a radially outer surface 54 and a radially inner surface 56. The ring curette 32 is difficult to accurately calibrate because the distal end 36 does not have a well defined tip. It should be appreciated that the ring curette 32 is shown for exemplary purposes, and that the calibration apparatus 48 may be implemented with other ring curette configurations and other medical devices.

The calibration apparatus 48 is removably attachable to the distal end 36 of the ring curette 32 in a known manner. The calibration apparatus 48 may be comprised of a material selected to be compatible with electro-magnetic tracking technology such a non-metallic material or a minimally conductive metal so that position characteristic field 44 (shown in FIG. 1) is not distorted. The calibration apparatus 48 includes a calibration member or device 58 adapted to engage a complementary feature such as the dimple 30 on the reference unit 14 (shown in FIG. 1). According to an exemplary embodiment, the member 58 is a "BB" which is defined for purposes of this disclosure as a spherical object. The calibration apparatus 48 is configured such that, when attached to the curette 32, the BB 58 is precisely aligned with and in close proximity to a predetermined portion (e.g., the bottom most portion 59) of the distal end 36. In the example illustrated in FIG. 2, the calibration apparatus 48 is designed so the BB 58 aligns with the bottom most portion 59 of the distal end 36, however, the BB 58 may alternatively be adapted to align with any other portion of the ring curette 32.

In one embodiment, the ring curette 32 is calibrated in the following manner. The calibration apparatus 48 is removably attached to the distal end 36 of the ring curette 32, and the calibration apparatus BB 58 is disposed in the reference unit dimple 30 (shown in FIG. 1). The calibration process 22 (shown in FIG. 1) is initiated and the ring curette body 50 is translated such that the BB 58 pivots within the dimple 30. After calibration is complete, the calibration apparatus 48 is removed from the ring curette 32 so that the ring curette 32 is not unnecessarily encumbered by a permanently attached calibration feature. By calibrating the ring curette 32 in the manner described, the position of the bottom most portion 59 of the distal end 36 may be conveyed to the surgeon in a convenient manner such as by a graphical representation superimposed on a patient image.

Figure 3:
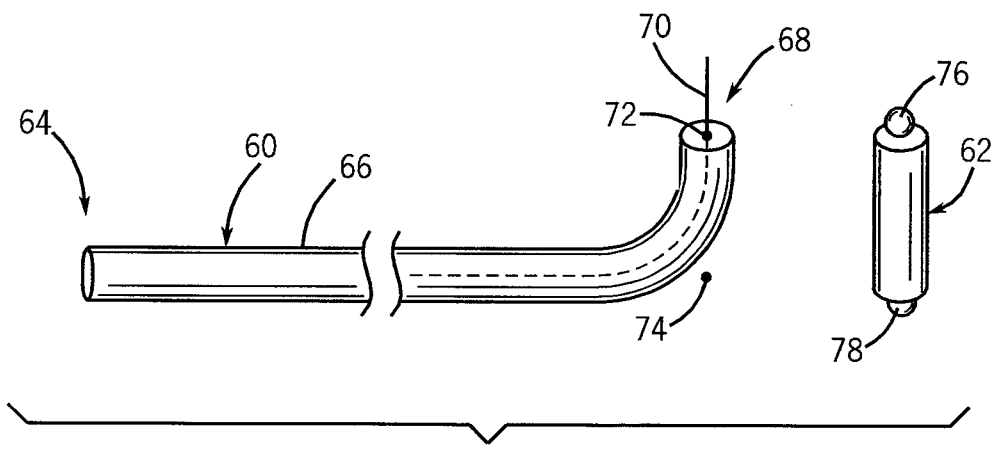
FIG. 3 is a perspective illustration of a catheter and a schematically depicted calibration apparatus in accordance with an exemplary embodiment.

Referring to FIG. 3, a catheter 60 is shown along with a schematic representation of a calibration apparatus 62. The catheter 60 includes a proximal end 64 to which the remote unit 16 (shown in FIG. 1) is attached, a cylindrical body 66, and a distal end 68 which is also the working end. The distal end 68 is angled at approximately 90 degrees relative to the body 66. A guide wire 70 is extendable from the front tip 72 of the distal end 68. A theoretical rear tip 74 may be defined to convey the trajectory along which the guide wire 70 is extendable. As the theoretical rear tip 74 is defined at a point in space it is difficult to accurately calibrate. It should be appreciated that the catheter 60 is shown for exemplary purposes, and that the calibration apparatus 62 may be implemented with other catheter configurations and other medical devices for a variety of medical and surgical applicable interventions.

The calibration apparatus 62 is removably attachable to the distal end 68 of the catheter 60 in a known manner. The calibration apparatus 62 may be comprised of a material selected to be compatible with electro-magnetic tracking technology such a non-metallic material or a minimally conductive metal so that position characteristic field 44 (shown in FIG. 1) is not distorted. The calibration apparatus 62 may include a front calibration member 76 and a rear calibration member 78 that are each adapted to engage a complementary feature such as the reference unit dimple 30 (shown in FIG. 1). According to an exemplary embodiment, the front member 76 and the rear member 78 each include a small spherical BB. The calibration apparatus is configured such that the front BB 76 aligns with the front tip 72, and the rear BB 78 aligns with the theoretical rear tip 74.

In one embodiment, the catheter 60 is calibrated in the following manner. The calibration apparatus 62 is removably attached to the distal end 68 of the catheter 60, and the front BB 76 is disposed in the reference unit dimple 30 (shown in FIG. 1). The calibration process 22 (shown in FIG. 1) is initiated and the catheter body 66 is translated such that the front BB 76 pivots within the dimple 30. The rear BB 78 is then disposed in the reference unit dimple 30. The calibration process 22 is initiated again and the catheter body 66 is translated such that the rear BB 78 pivots within the dimple 30. After calibration of both the front BB 76 and the rear BB 78 is complete, the calibration apparatus 62 is removed from the catheter 60 so that the catheter 60 is not unnecessarily encumbered by a permanently attached calibration feature. By calibrating the catheter 60 in the manner described, the position of distal end 68 and the trajectory of the guide wire 70 may be conveyed to the surgeon in a convenient manner such as by a graphical representation superimposed on a patient image.

Figure 4A:
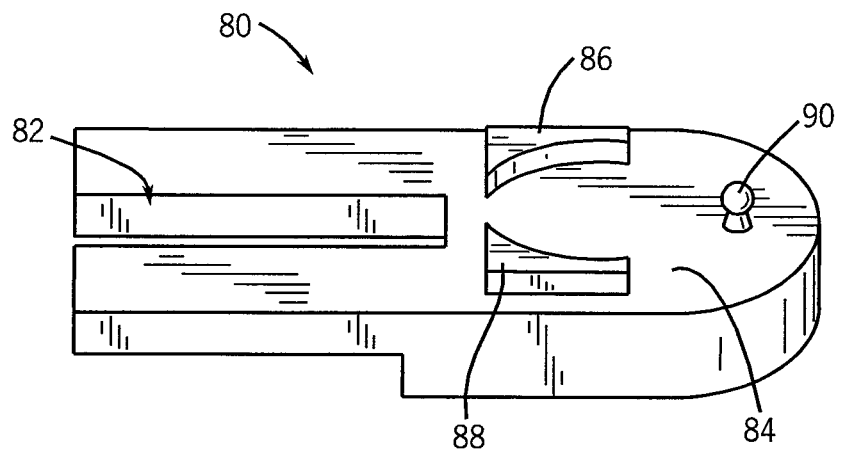
FIG. 4a is a perspective illustration of a calibration apparatus in accordance with an exemplary embodiment.
Figure 4B:
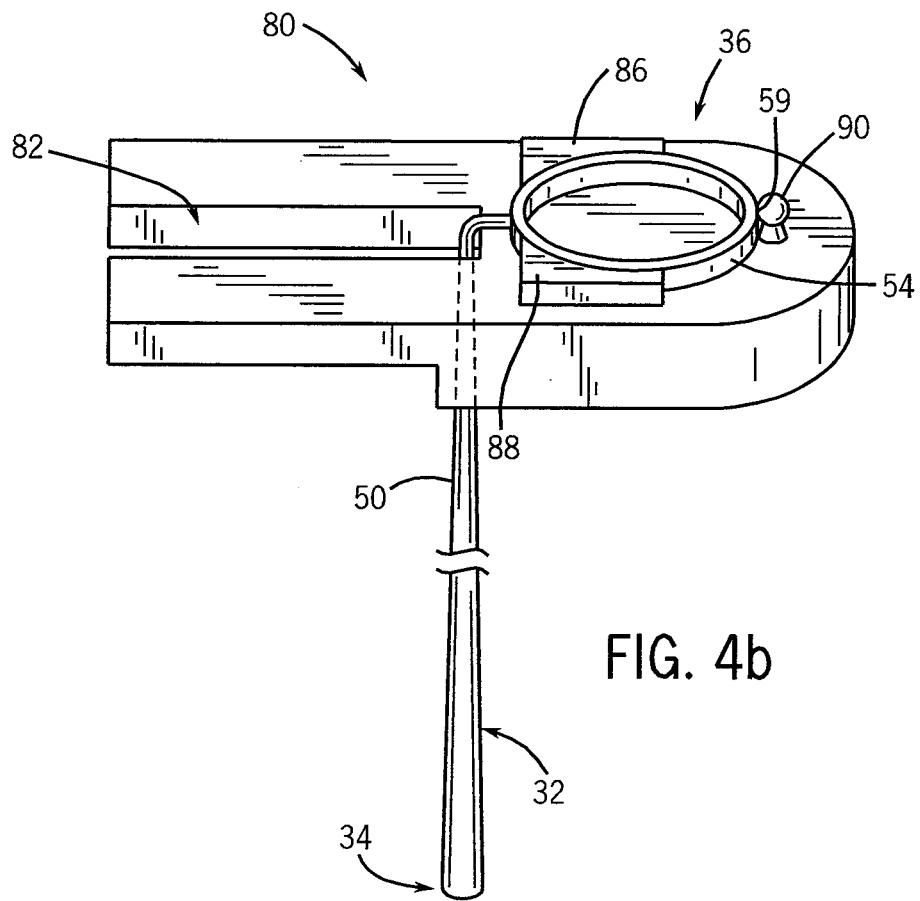
FIG. 4b is a perspective illustration of the calibration apparatus of FIG. 4a attached to the ring curette of FIG. 2.

FIGS. 4a-4b respectively illustrate a calibration apparatus 80 in accordance with an embodiment of the invention, and the calibration apparatus 80 as it is attached to the ring curette 32. The calibration apparatus 80 may be comprised of a material selected to be compatible with electro-magnetic tracking technology such a non-metallic material or a minimally conductive metal so that position characteristic field 44 (shown in FIG. 1) is not distorted.

Referring to FIG. 4a, a perspective view of the calibration apparatus 80 is shown. The calibration apparatus 80 defines a clearance slot 82, and includes a locating surface 84, first and second locating blocks 86, 88, and a calibration member 90. The member 90 will be described hereinafter as a BB, however, other members may alternatively be implemented.

Referring now to FIG. 4b, the calibration apparatus 80 is shown attached to the ring curette 32. The calibration apparatus 80 is retained on the ring curette 32 by an interference fit therebetween. More precisely, the distal end 36 is interference fit between the first locating block 86, the second locating block 88, and the BB 90. The clearance slot 82 accommodates the body 50 of the ring curette 32 during attachment. The rearward edge 52 (shown in FIG. 2) of the distal end 36 rests on the locating surface 84 (shown in FIG. 4a). The first and second locating blocks 86, 88 engage and thereby locate first and second portions of the radially outer surface 54. The BB 90 engages and thereby locates a third portion of the radially outer surface 54. By locating the calibration apparatus 80 on the distal end 36 of the ring curette 32 in the manner described, the BB 90 can be precisely positioned with respect to a predetermined portion (e.g., the bottom most portion 59) of the distal end 36.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A navigation system for a medical device to be at least partially inserted into a patient during a surgical procedure, the system comprising:
 a reference unit configured to attach to a patient;
 a field generator disposed within the reference unit, the field generator creates an electromagnetic field about the field generator;

a remote unit configured to attach to a proximal end of the medical device, the remote unit generates a signal based upon the location of the remote unit within the electromagnetic field;

a processor connected to the remote unit to receive the signal from the remote unit, the signal being indicative of the position and/or the orientation of the remote unit relative to the reference unit; and a calibration apparatus removably attachable to a distal end of the medical device, said calibration apparatus having a calibration member that aligns with a work end of the medical device when the calibration apparatus is attached to the medical device;

wherein the processor determines a location and an orientation of said remote unit with respect to the reference unit when the calibration member is physically engaged with the reference unit to calibrate the navigation system by relating the distal end of the medical device represented by the calibration apparatus to the proximal end of the medical device; and wherein the calibration apparatus prohibits use of the medical device for the surgical procedure when attached to the distal end of the medical device, therefore the calibration apparatus is attached to the distal end of the medical device to calibrate the navigation system and removed from the medical device for the surgical procedure.

2. The navigation system of claim 1, wherein said reference unit includes a reference feature that receives the calibration member.

3. The navigation system of claim 1, wherein said reference unit is an electromagnetic field generator mounted to the patient.

4. The navigation system of claim 3, wherein the processor determines a location of the remote unit within an electromagnetic field generated by the reference unit.

5. The navigation system of claim 4 wherein the remote unit comprises at least one field sensor that produces a signal indicative of a location of the remote unit within the electromagnetic field, wherein the signal is sent to the processor.

6. The navigation system of claim 1, wherein the calibration member is a first calibration member that aligns with a front tip of the distal end and said calibration apparatus further includes a second calibration member that aligns with a back tip of the distal end of the medical device when the calibration apparatus is attached to the medical device.

7. A method for electromagnetically determining the location of a predetermined portion of a medical device configured for insertion into a patient, the medical device comprising an electromagnetic remote unit, said method comprising:

providing a calibration apparatus having a first calibration member, the calibration apparatus being configured for removable attachment to a distal end of the medical device;

attaching the calibration apparatus to the medical device such that the first calibration member aligns with a work end of the medical device, the first calibration member representing a front tip of the work end;

providing a reference unit secured to the patient, the reference unit comprising a field generator;

generating an electromagnetic field from the field generator of the reference unit;

determining a location of the remote unit with respect to the reference unit by locating the remote unit within the electromagnetic field generated by the reference unit;

physically engaging the reference unit with the first calibration member;

calibrating the medical device by locating a position and an orientation of the remote unit with respect to the reference unit and the first calibration member; and removing the calibration apparatus from the medical device after calibrating the medical device and before the medical device is used in a surgical procedure such that the work end of the medical device is inserted into the patient without encumbrance by the calibration apparatus or the calibration member.

8. The method of claim 7, further comprising engaging a dimple in the reference unit with the calibration member; and pivoting the medical device about the calibration member within the dimple in the reference unit.

9. The method of claim 8, further comprising rigidly attaching the reference unit to a patient.

10. The method of claim 9, wherein said providing a calibration apparatus having a calibration member includes providing an apparatus having a first calibration member and a second calibration member.

11. A medical device navigation system comprising:

a medical device configured to be inserted into a patient during a surgical procedure, the medical device having a proximal end and a distal end opposite the proximal end, the distal end being a working end without a well-defined tip;

a calibration apparatus removably attachable to the distal end of the medical device such that when the calibration apparatus is attached to the distal end, a first calibration member of the calibration apparatus defines a tip of the medical device;

a reference unit configured to attach to the patient and configured with a complementary feature to receive the first calibration member of the calibration apparatus, a field generator within the reference unit generates a position characteristic field;

a remote unit attached to the proximal end of the medical device, the remote unit produces a signal indicative of the position of the remote unit within the position characteristic field of the reference unit; and a processor connected to the remote unit, the processor receives the signal from the remote unit;

wherein the processor determines a position and an orientation of the distal end of the medical device relative to the proximal end of the medical device by determining the position of the remote unit within the position characteristic field when the first calibration member physically engages the complimentary feature of the reference unit.

12. The system of claim 11 wherein the complimentary feature of the reference unit is a dimple in the reference unit that approximates the center of the position characteristic field.

13. The system of claim 11 wherein the medical device is a surgical instrument.

14. The system of claim 11 wherein the medical device is a surgical implant.

15. The system of claim 11 wherein the calibration apparatus is removed from the medical device after calibration and before the medical device is inserted into the patient.

16. The system of claim 11 wherein the first calibration member defines a front tip of the medical device, and further comprising a second calibration member of the calibration apparatus, the second calibration member defines a back tip of the medical device, when the calibration apparatus is attached to the distal end of the medical device.

17. The system of claim 16 wherein the processor further determines a trajectory of the distal end of the medical device by determining the position of the remote unit within the position characteristic field when the second calibration member engages the complimentary feature of the reference unit, and wherein the processor identifies the trajectory of the distal end as a line connecting a determined position of the first calibration member with a determined position of the second calibration member.

18. The system of claim 11 wherein the remote unit comprises at least one field sensor that produces the signal indicative of the position of the remote unit.

19. A method for tracking the position and orientation of a medical device during a surgical procedure, the medical device having a distal end and a proximal end opposite the distal end, and the surgical procedure inserts at least the distal end of the medical device into a patient, the method comprising:

providing an electromagnetic remote unit attached to the proximal end of the medical device;

securing an electromagnetic reference unit to the patient;

generating an electromagnetic field with the reference unit;

removably attaching a calibration apparatus to the distal end of the medical device, a calibration member of the calibration apparatus aligning with a front tip of the distal end;

physically engaging the reference unit with the calibration member;

locating with a processor a position and an orientation of the remote unit within the electromagnetic field and with respect to the engaged reference unit and calibration member by processing the received signal with the processor;

calibrating a navigation system for the medical device by relating the position and orientation of the remote unit to the calibration member;

removing the calibration apparatus from the distal end of the medical device; and inserting the distal end of the medical device into the patient to perform the surgical procedure.

20. The method of claim 19 further comprising:

sensing the electromagnetic field with at least one field sensor in the electromagnetic remote unit; and providing a signal indicative of the sensed electromagnetic field from the at least one field sensor to the processor.

* * * * *